US00PP34990P2

(12) United States Plant Patent
Zaiger et al.

(10) Patent No.: US PP34,990 P2
(45) Date of Patent: Feb. 21, 2023

(54) APPLE TREE NAMED 'ZEEAPPLE-1'

(50) Latin Name: *Malus domestica*
Varietal Denomination: Zeeapple-1

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 17/803,462

(22) Filed: Jul. 22, 2022

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
CPC ... A01H 5/08; A01H 5/00; A01H 5/02; A01H 6/74; A01H 6/7418
See application file for complete search history.

(56) References Cited

U.S. PATENT DOCUMENTS

PP7,880 P * 6/1992 Cripps ..... Plt./161

* cited by examiner

*Primary Examiner* — June Hwu

(57) ABSTRACT

A new and distinct variety of apple tree. The following features of the tree and its fruit are characterized with the tree budded on 'M.7' Apple Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Fruit with a high degree of attractive red skin color.
4. Fruit ripening in the early maturing season.
4. Fruit with very good flavor and eating quality.
5. Fruit with good storage and shipping ability.

1 Drawing Sheet

Botanical designation: *Malus domestica.*
Variety denomination: 'Zeeapple-1'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, apples, almonds and interspecifics are exemplary. It was against this background of our activities that the present variety of apple tree was originated and asexually reproduced by us in our experimental orchard located near Modesto, Stanislaus County, Calif.

Prior Varieties

Among the existing varieties of apple trees, which are known to us, and mentioned herein, 'Cripps Pink' Apple (U.S. Plant Pat. No. 7,880) and our proprietary non-patented apple seedling selections '49ZM839', '4MK592', '44ZG718' and '44ZM103'.

ORIGIN OF THE VARIETY

The new and distinct variety of apple tree was originated by us in our experimental orchard located near Modesto, Calif. as a first generation cross between our proprietary non-patented apple seedlings '49ZM839' and '4MK592'. The seed parent (49ZM839) originated as an open pollinated seedling from our non-patented seedling selection '44ZG718'. The pollen parent (4MK592) originated as an open pollinated seedling from our non-patented seedling selection '44ZM103'. A large group of these first generation seedlings were grown and budded onto older trees of 'M.7' Apple Rootstock (non-patented) to accelerate fruit production for evaluation. Under close and careful observation, one such seedling, which is the present variety, exhibited desirable fruit and tree characteristics and was selected in 2017 for additional asexual propagation and commercialization.

ASEXUAL REPRODUCTION OF THE VARIETY

In 2017 asexual reproduction of the new and distinct variety of apple tree was by budding to 'M.7' Apple Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of apple tree is of large size, vigorous, upright growth and a regular and productive bearer of early maturing, large size fruit. The fruit is further characterized by its attractive red skin color with very good flavor and eating quality. In comparison to its proprietary non-patented apple seed parent '49ZM839' the fruit of the new variety is larger in size, has a higher degree of red skin color and is approximately 30 days earlier in maturity. In comparison to its proprietary non-patented apple pollen parent '4MK592' the fruit of the new variety has crispier fruit texture, larger in size and is approximately 5 days earlier in maturity. In comparison to 'Cripps Pink' Apple (U.S. Plant Pat. No. 7,880) the fruit of the new variety is approximately 90 days earlier in maturity.

DESCRIPTION OF THE PHOTOGRAPH

The accompanying color photographic illustration shows typical specimens of the foliage and fruit of the present new apple variety. The illustration shows the upper and lower surface of the leaves, an exterior and sectional view of a single fruit divided in a transverse cross section to show flesh color, core and the seeds remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of apple tree, its flowers, foliage and fruit, as based on observations of 9 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright to spreading, crotch angle approximately 45°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 6 consecutive years. No alternate bearing observed.

*Fertility*.—Self fertile, sets fruit under bag.

*Density*.—Medium dense, usually pruned to vase shape to increase air movement and sunlight to enhance fruit color and health of fruit spurs.

*Hardiness*.—Hardy in all fruit growing areas of California. Tree grown in USDA Hardiness Zone 9. Winter chilling requirement approximately 400 hours at or below 45° F.

Trunk:

*Size*.—Medium, average circumference 29.2 cm at 25.4 cm above ground on a 9 year old tree.

*Stocky*.—Medium stocky.

*Texture*.—Smooth.

*Color*.—Varies from 10YR 6/2 to 10YR 5/2.

Branches:

*Size*.—Medium. Average circumference 8.6 cm at 1.2 meters above ground. Crotch angle approximately 45°, increases with heavy crop load.

*Surface texture*.—New growth relatively smooth. Mature growth relatively smooth.

*Lenticels*.—Average number 23 in a 25.8 square cm area. Average length 3.1 mm. Average width 1.2 mm. Color varies from 10YR 6/8 to 10YR 5/8.

*Color*.—New growth varies from 2.5YR 2/2 to 2.5YR 2/4 as influenced by pubescence. Light to moderate pubescence covers 100% of surface area of new growth. Pubescence color varies N 9.5/(white) to 5GY 9/1. Mature growth varies from 7.5YR 5/2 to 7.5YR 3/2, varies with age of growth.

Leaves:

*Size*.—Medium. Average length 70.5 mm. Average width 38.2 mm.

*Form*.—Elliptical.

*Apex*.—Acuminate.

*Base*.—Cuneate.

*Margin*.—Serrate.

*Thickness*.—Medium-thick.

*Surface texture*.—Upper surface relatively smooth, slight indentations over midrib and leaf veins. Lower surface relatively smooth, except for small ridges created by midrib and pinnate venation. Upper surface glabrous. Lower surfaces finely pubescent.

*Petiole*.—Average length 24.5 mm. Average width 1.9 mm. Longitudinally grooved. Surface — light pubescence. Color varies from 2.5GY 7/6 to 2.5GY 6/6.

*Glands*.—None present.

*Stipules*.—Average number 2. Average length 7.9 mm. Edges — smooth. Surface — pubescent. Color varies from 2.5GY 7/2 to 2.5GY 8/2.

*Color*.—Upper surface varies from 7.5GY 4/4 to 7.5GY 2/4. Lower surface varies from 7.5GY 7/2 to 7.5GY 5/2. Midvein color varies from 2.5GY 8/4 to 2.5GY 7/4.

Flower buds:

*Size*.—Medium. Average length 13.0 mm. Average diameter 6.8 mm.

*Hardiness*.—Hardy with respect to California winters.

*Density*.—Light density.

*Form*.—Conical, becoming elongated just before opening.

*Pedicel*.—Average length 10.5 mm. Average width 0.9 mm. Surface- pubescent. Color varies from 5GY 5/4 to 7.5GY 7/2.

*Color*.—Varies from 10RP 4/12 to 7.5RP 4/10.

*Number of buds per spur*.—Average number 1.

Flowers:

*Blooming period*.—Date of First Bloom Mar. 4, 2022. Date of Petal Fall Mar. 17, 2022, varies slightly with climatic conditions.

*Size*.—Medium to large. Average height 10.8 mm. Average diameter 24.9 mm.

*Petals*.—Number — normally five, alternately arranged to sepals. Size — medium. Average length 14.5 mm. Average width 9.9 mm. Petal apex — rounded. Petal base — truncate. Form — elliptical. Arrangement — overlapping. Margin — sinuate. Color varies from 7.5RP 7/4 to 7.5RP 5/8, fades with age of flower. Both upper and lower surfaces glabrous.

*Sepals*.—Number — normally five, alternately arranged to petals. Size — medium to large. Average length 7.2 mm. Average width 2.7 mm. Apex — triangular. Margin — entire. Color — upper surface varies from 7.5GY 7/4 to 7.5GY 6/4. Lower surface varies from 7.5GY 8/4 to 7.5GY 7/4. Both upper and lower surfaces pubescent.

*Stamens*.—Average number per flower 17. Average filament length 8.7 mm. On average, the stamens are above the height of the petals. Filament color N 9.5/(white). Anther color varies from 5Y 8.5/6 to 5Y 8/8.

*Pollen*.—Self fertile, sets fruit under bag. Color varies from 5Y 7/10 to 5Y 7/12.

*Pistil*.—Number — normally 5. Average length 7.4 mm. Position of stigma an average of 1.8 mm below anthers. Style surface is glabrous. Ovary base is pubescent. Color varies from 2.5GY 5/8 to 5GY 6/6.

*Fragrance*.—Slight aroma.

*Color*.—Varies from 7.5RP 7/4 to 7.5RP 4/6.

*Pedicel*.—Average length 12.1 mm. Average width 1.4 mm. Color varies from 7.5GY 6/2 to 7.5GY 6/4.

*Number flowers per flower bud*.—Average number 5.

Fruit:

*Maturity when described*.—Firm ripe and ready for consumption.

*Date of first picking*.—Jul. 8, 2022.

*Date of last picking*.—Jul. 18, 2022, varies slightly with climatic conditions.

*Size*.—Large. Average diameter axially 75.2 mm. Average transversely 88.5 mm. Average weight 255.1 grams, varies slightly with fertility of the soil, amount of thinning and climatic conditions.

*Form*.—Globose to slightly elongated.

*Ventral surface*.—Ribbing — absent.

*Basin cavity*.—Average width 25.5 mm. Average depth 19.3 mm. Smooth surface to slightly ribbed. Basin cavity shape — conical. Sepals present with erect tips, mostly closed.

*Stem cavity*.—Rounded to slightly elongated. Average depth 9.5 mm. Average diameter 7.2 mm.

Stem:

*Size*.—Large. Average length 15.6 mm. Average diameter 2.2 mm.

*Color*.—Varies from 10Y 5/6 to 7.5Y 6/8.

Flesh:

*Ripens*.—Evenly.

*Texture*.—Crisp, firm.

*Firmness*.—Firm, comparable to other commercial apple varieties.

*Aroma*.—Slight.

*Eating quality*.—Very good.

*Flavor*.—Sweet, good balance between acid and sugar.

*Juice*.—Moderate amount, enhances flavor.

*Acidity*.—Not available.

*Brix*.—Average Brix 15.8°, varies slightly with amount of fruit per tree and climatic conditions.

*Flesh color*.—Varies from N 9.5/(white) to 5Y 8.5/4.

*Core*.—Medium position. Color varies from N 9.5/(white) to 2.5Y 8.5/4.

Skin:

*Thickness*.—Medium thin.

*Surface*.—Smooth, medium glossy with medium cutical wax.

*Bloom*.—Wanting.

*Tendency to crack*.—None.

*Color*.—Ground color varies from 7.5Y 7/6 to 7.5Y 7/8. Overspread with 7.5R 4/10 to 7.5R 4/12. Skin lenticels present, round. Average number 34 in a square inch section. Average 1.0 mm in diameter. Lenticel color varies from 7.5Y 7/6 to 7.5Y 7/8.

*Tenacity*.—Tenacious to the flesh.

*Astringency*.—None.

Seeds:

*Size*.—Small, average number per fruit — 10. Average length 7.4 mm. Average width 3.3 mm. Average depth 2.3 mm.

*Form*.—Ovate.

*Viability*.—Viable, complete embryo development.

*Color*.—Varies from 5YR 3/6 to 7.5YR 3/6.

Use:

*Dessert*.—Market — local and long distance.

Keeping quality: Good, held firm in typical cold storage conditions for 3 months without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of apple tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of apple tree (*Malus domestica*) named 'Zeeapple-1', substantially as illustrated and described.

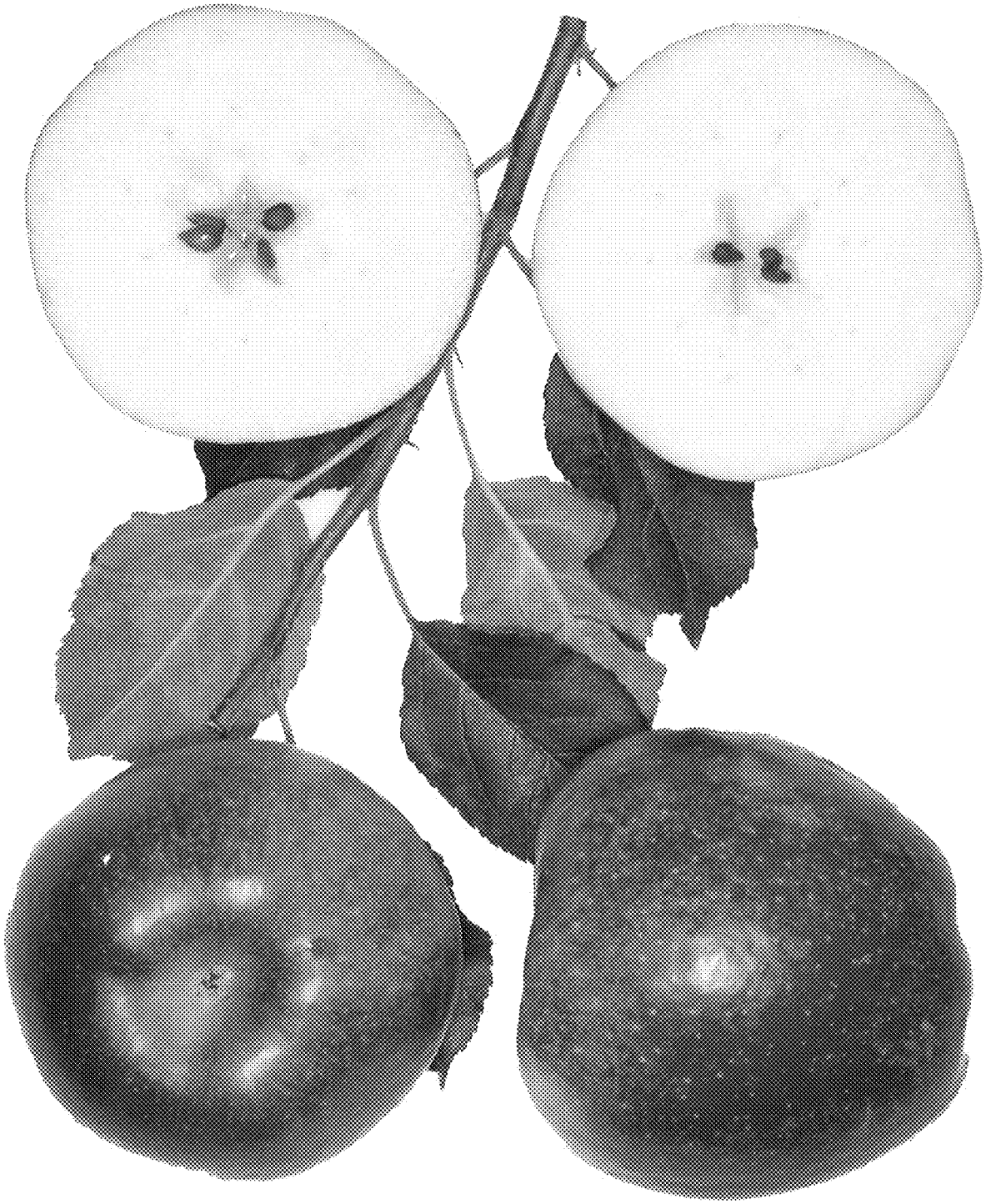

* * * * *